United States Patent
Childress

(10) Patent No.: US 11,382,993 B2
(45) Date of Patent: Jul. 12, 2022

(54) PORTABLE SANITIZING SYSTEMS AND METHODS WITH RANGE GUIDANCE

(71) Applicant: THE BOEING COMPANY, Chicago, IL (US)

(72) Inventor: Jamie J. Childress, Mercer Island, WA (US)

(73) Assignee: THE BOEING COMPANY, Chicago, IL (US)

( * ) Notice: Subject to any disclaimer, the term of this patent is extended or adjusted under 35 U.S.C. 154(b) by 106 days.

(21) Appl. No.: 17/039,011

(22) Filed: Sep. 30, 2020

(65) Prior Publication Data

US 2021/0361793 A1    Nov. 25, 2021

Related U.S. Application Data

(60) Provisional application No. 63/027,869, filed on May 20, 2020.

(51) Int. Cl.
*A61L 2/10*    (2006.01)

(52) U.S. Cl.
CPC ..................... *A61L 2/10* (2013.01)

(58) Field of Classification Search
CPC .... A61L 2/10; A61L 2202/11; A61L 2202/16; A61L 2202/25; A61L 2202/26
See application file for complete search history.

(56) References Cited

U.S. PATENT DOCUMENTS

| | | | |
|---|---|---|---|
| 11,007,292 | B1 | 5/2021 | Grenon |
| 2010/0104471 | A1 | 4/2010 | Harmon |
| 2011/0054310 | A1 | 3/2011 | Taylor |
| 2016/0114067 | A1 | 4/2016 | Dobrinsky |
| 2018/0117191 | A1 | 5/2018 | Shell |
| 2019/0255201 | A1 | 8/2019 | Rosen |
| 2021/0162079 | A1 | 6/2021 | Rosen |

FOREIGN PATENT DOCUMENTS

| | | |
|---|---|---|
| JP | 2019 073479 | 5/2019 |
| WO | WO 2021/150734 | 7/2021 |

OTHER PUBLICATIONS

Extended European Search Report for EP 21174471.9-1012, dated Nov. 19, 2021.
U.S. Appl. No. 17/016,466, filed Sep. 10, 2020.
U.S. Appl. No. 29/735,235, filed May 19, 2020.
U.S. Appl. No. 17/026,414, filed Sep. 21, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.

*Primary Examiner* — Britt D Hanley
(74) *Attorney, Agent, or Firm* — The Small Patent Law Group LLC; Joseph M. Butscher

(57) ABSTRACT

A sanitizing head includes a housing and multiple range light sources. The housing retains an ultraviolet (UV) lamp, and UV light emitted from the UV lamp exits through a front end of the housing. The range light sources are secured to the housing and arranged in one or more pairs. The range light sources in each pair of the one or more pairs are oriented relative to each other to emit respective light beams that converge at a predetermined distance in front of the UV lamp.

21 Claims, 12 Drawing Sheets

PORTABLE SANITIZING SYSTEMS AND METHODS WITH RANGE GUIDANCE

CROSS-REFERENCE TO RELATED APPLICATIONS

This application relates to and claims priority benefits from U.S. Provisional Patent Application No. 63/027,869, entitled "Portable Sanitizing Systems and Methods with Range Guidance," filed May 20, 2020, which is hereby incorporated by reference in its entirety.

FIELD OF THE DISCLOSURE

Embodiments of the present disclosure generally relate to sanitizing systems, such as may be used to sanitize structures and areas within vehicles, such as commercial aircraft.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

In order to sanitize a surface of a structure, a known UV light sterilization method emits a broad spectrum UVC light onto the structure. However, UVC light typically takes a significant amount of time (for example, three minutes) to kill various microbes. Further, various microbes may not be vulnerable to UVC light. That is, such microbes may be able to withstand exposure to UVC light.

Disinfection is a function of radiation energy per area imparted to the target surface. The disinfection irradiance depends on both the proximity of the UV light source to the target surface and the time of illumination. Disinfection effectiveness decreases with increased range or distance between the UV light source and the target surface beyond a certain threshold range. If the UV light source is too far from the target surface the dose of energy provided to a certain area of the target surface may be lower than required to kill a targeted pathogen or microbe. Typically, a user manipulating the UV light source estimates the proper range between the light source and the target surface, but this technique is likely to be inaccurate and inconsistent, especially if the light source is located a significant distance from the user. As a result, the sanitization process may be ineffective at providing consistent disinfection across a large area. A physical spacer could be used that extends a predetermined distance from the light source to the target surface to maintain the desired proximity range, but the inherent physical contact with the target surface could potentially spread pathogens and could also obstruct the UV light from reaching the target.

SUMMARY OF THE DISCLOSURE

A need exists for a system and a method for efficiently providing ranging guidance which assists the user to maintain the UV light source at a desirable distance from the target disinfecting surface to provide reliable, consistent sanitization.

With those needs in mind, certain embodiments of the present disclosure provide a portable sanitizing system that includes range guidance. The portable sanitizing system includes a sanitizing head that has a housing and multiple range light sources. The housing retains an ultraviolet (UV) lamp, and UV light emitted from the UV lamp exits through a front end of the housing. The range light sources are secured to the housing and arranged in one or more pairs. The range light sources in each pair of the one or more pairs are oriented relative to each other to emit respective light beams that converge at a predetermined distance in front of the UV lamp.

Optionally, the housing may include a shroud that defines a front opening. The range light sources may be spaced apart along an exposed perimeter edge of the shroud at the front opening. The exposed perimeter edge may have multiple segments, and the range light sources in each respective pair of the one or more pairs are disposed on a common segment of the multiple segments. Optionally, the exposed perimeter edge may be rectangular with two longer segments that extend between two shorter segments, and the range light sources may be disposed on at least the two longer segments. Optionally, the one or more pairs of range light sources may include at least four pairs, such that at least two of the pairs are disposed on each of the two longer segments of the exposed perimeter edge.

Optionally, the predetermined distance may be no less than 1 inch and no greater than 6 inches. Optionally, the light beams emitted by the range light sources in each pair have different colors. Optionally, the range light sources may be light emitting diodes (LEDs) that have a divergence no greater than 10 degrees. Optionally, the range light sources in each pair may be oriented at an angle in a range between 20 degrees and 60 degrees relative to each other.

Optionally, the one or more pairs may include multiple pairs arranged in a first subset of one or more pairs and a second subset of one or more pairs. The range light sources in each pair within the first subset are oriented at a first relative angle, and the range light sources in each pair within the second subset are oriented at a second relative angle that is different from the first relative angle. The first relative angle may be at least 40 degrees and no greater than 60 degrees, and the second relative angle may be at least 20 degrees and less than 40 degrees. Optionally, the first relative angle may be approximately 53 degrees, and the second relative angle may be approximately 28 degrees.

Optionally, the UV lamp may be configured to emit UV light in the far UV range, such that the UV light has a wavelength between 200 nm and 230 nm. Optionally, the UV light may have a wavelength of approximately 222 nm. Optionally, the UV lamp may be configured to emit UV light in the UV-C range, such that the UV light has a wavelength between 230 nm and 280 nm. Optionally, the UV light may have a wavelength of approximately 254 nm.

In at least one embodiment, a portable sanitizing method is provided that includes emitting ultraviolet (UV) light from a sanitizing head including a housing an a UV lamp. The method also includes emitting a first light beam from a first range light source on the sanitizing head and a second light beam from a second range light source on the sanitizing head to cause the first and second light beams to converge at a predetermined distance from the UV lamp.

In at least one embodiment, a sanitizing head is provided that includes a housing and multiple range light sources. The housing retains an ultraviolet (UV) lamp configured to emit UV light. The housing includes a shroud that defines a front opening. The range light sources are secured to the housing and spaced apart along an exposed perimeter edge of the shroud at the front opening. The range light sources are arranged in one or more pairs. The range light sources in each pair are oriented relative to each other to emit respective light beams that converge at a predetermined distance in front of the UV lamp. The range light sources are light emitting diodes (LEDs) that have a divergence no greater than 10 degrees, and the light beams emitted by the range light sources in each pair have different colors.

DETAILED DESCRIPTION OF THE DISCLOSURE

Figure 1:
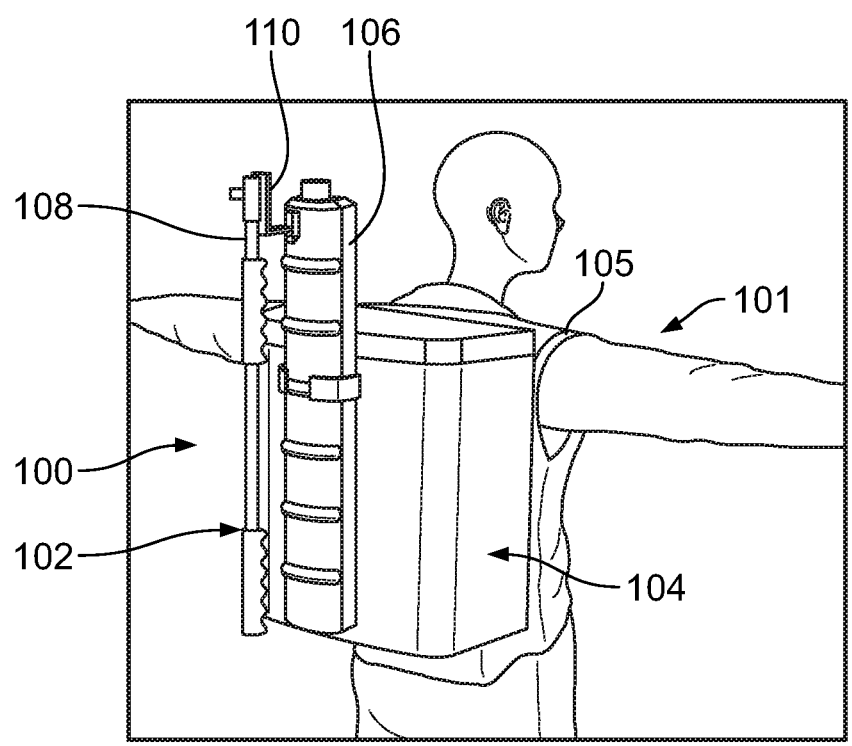
FIG. 1 illustrates a perspective view of a portable sanitizing system worn by an individual, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method that includes a UV lamp that emits UV light which neutralizes (such as kills) microbes (for example, viruses and bacteria), while posing no risk to humans. The UV lamp may be used within an internal cabin to decontaminate and kill pathogens. Embodiments of the present disclosure provide safer and more effective sanitation as compared to certain known UV systems. The sanitizing system includes a sanitizing head that is portable. The sanitizing head can be manipulated by a user, such as a human or robot, that waves the sanitizing head within the internal cabin to emit UV light onto surfaces within the cabin. The sanitizing head has a housing and an ultraviolet (UV) lamp and range light sources mounted to the housing. The range light sources may be positioned along the length of the housing on both sides of the UV lamp.

The range light sources are configured to help the user maintain a correct range or distance between the UV lamp and the target surface being sanitized to provide effective disinfection of the target surface. For example, the range light sources are arranged in pairs. The two range light sources in each pair are oriented towards each other such that the respective light beams emitted from the two light sources converge at a location in front of the sanitizing head. The two range light sources in each pair are oriented such that the light beams converge at a predetermined distance in front of the sanitizing head that is associated with effective disinfection. The convergence of the lights is visible on the target surface when the sanitizing head is located at the predetermined distance from the target surface which indicates to the user manipulating the sanitizing head that the sanitizing head is properly positioned relative to the target surface to provide effective disinfection of the target surface. If the sanitizing head is located too close to the target surface and/or too far from the target surface, the light beams emitted from the first and second range light source of the pair are spaced apart (e.g., do not converge) on the target surface. The user can see that the two lights are non-converging on the target surface which indicates that the sanitizing head is not properly positioned relative to the target surface for effective disinfection. The range light sources therefore provide active range guidance for the user manipulating the sanitizing head by providing a visual indication of whether or not the sanitizing head is at a correct distance from the target surface.

The range light sources also serve to frame or define the edges of the surface area receiving UV light (e.g., radiation). For example, the UV light emitted from the UV lamp may be difficult or impossible to see on the surface of the structure being disinfected, so the visible light emitted by the range light sources visually indicate the region or surface area of the structure that currently receives UV light. The range light sources may emit a series of small light markers that frame the region being illuminated, without emitting light into a center of the illuminated area. The light emitted by the range light sources does not interfere with the disinfection process.

Certain embodiments of the present disclosure provide a portable sanitizing system for disinfecting surfaces, such as within an internal cabin of a vehicle. The portable sanitizing system includes a wand assembly. The wand assembly may include a housing, a UV lamp, a reflector, mounts to secure the UV lamp to the housing, an inlet to allow air to be drawn across the UV lamp, and a handle for manually grasping and manipulating the wand assembly. The wand assembly, or some components thereof, is referred to herein as a sanitizing head. Optionally, the wand assembly may be coupled, via a hose and/or one or more cables, to a power source, such as a backpack assembly, a carrying case, a wheeled cart, a stationary power source, or the like. For example, the power source can include a main body or housing, one or more batteries (such as rechargeable batteries), a plug for recharging the one or more batteries, an air blower, a carbon filter, an exhaust vent, and/or the like.

FIG. 1 illustrates a perspective view of a portable sanitizing system 100 worn by an individual or user 101, according to an embodiment of the present disclosure. The portable sanitizing system 100 includes a wand assembly 102 coupled to a backpack assembly 104 that is removably secured to the individual through a harness 105. The wand assembly 102 includes a sanitizing head 106 coupled to a handle 108. In at least one embodiment, the sanitizing head 106 is moveably coupled to the handle 108 through a coupler 110. In another embodiment, the sanitizing head 106 has an integral handle instead of, or in addition to, the handle 108 coupled via the coupler 110. As shown in FIG. 1, the wand assembly 102 is in a stowed position. In the stowed position, the wand assembly 102 is removably secured to a portion of the backpack assembly 104, such as through one or more tracks, clips, latches, belts, ties, and/or the like. In another embodiment, the portable sanitizing system 100 may include a wheeled assembly that rolls along the ground or a carrying case connected to the wand assembly 102 via a hose instead of the backpack assembly 104. In still another embodiment, only the wand assembly 102 is portable and is connected to a stationary assembly via a hose 122 (shown in FIG. 2). In another embodiment, the wand assembly 102 may be coupled on a device, such as a robot that moves along an interior cabin. The wand assembly 102 can be controlled indirectly via controlling the movement of the robot, rather than carrying and manually manipulating the wand assembly 102.

Figure 2:
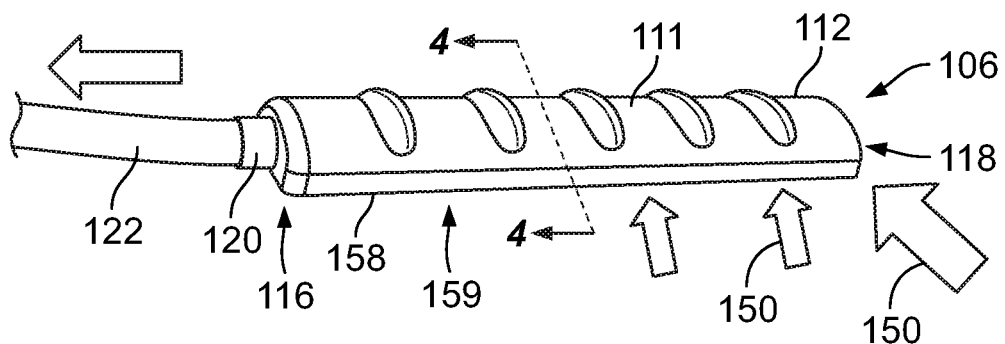
FIG. 2 illustrates a perspective top view of a sanitizing head, according to an embodiment of the present disclosure.
Figure 3:
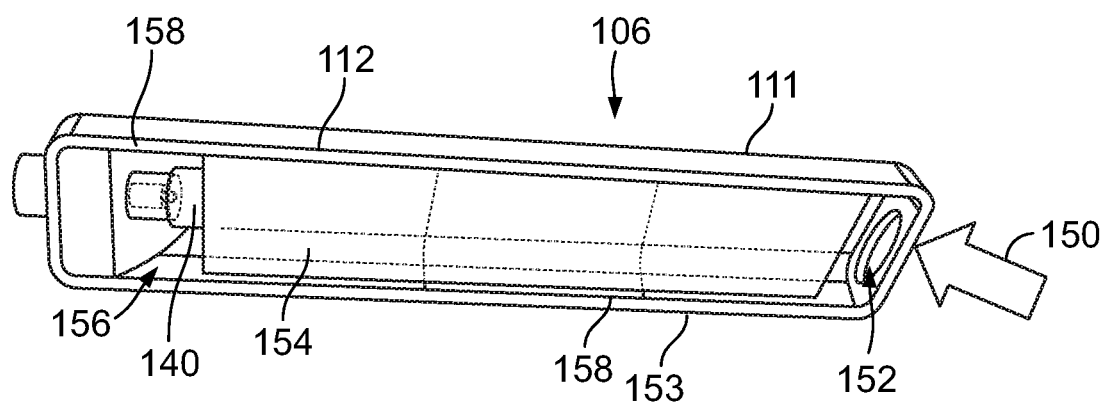
FIG. 3 illustrates a perspective bottom view of the sanitizing head of FIG. 2.
Figure 4:
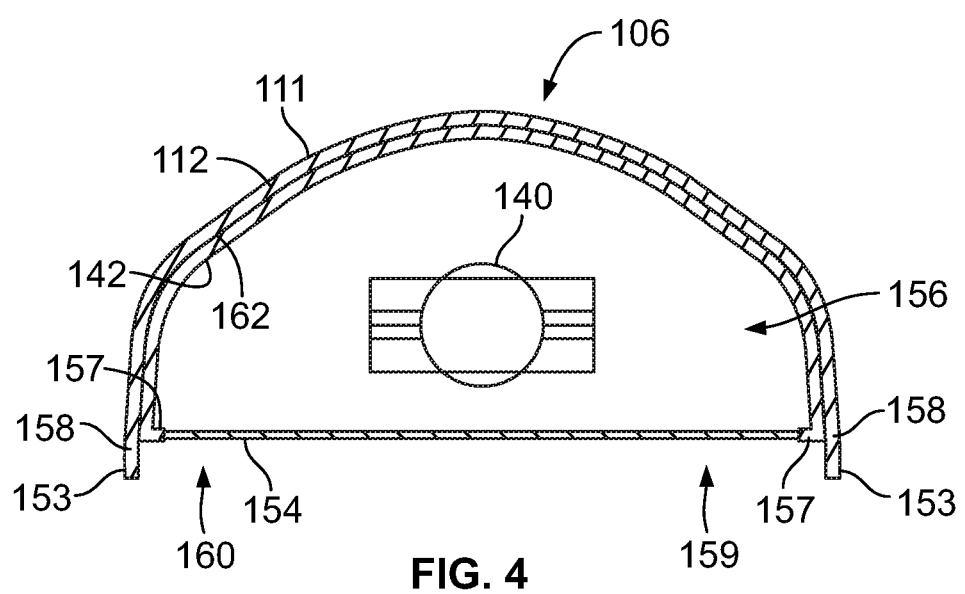
FIG. 4 illustrates an axial cross-sectional view of the sanitizing head through line 4-4 of FIG. 2.

FIG. 2 illustrates a perspective top view of the sanitizing head 106 of the wand assembly 102 according to an embodiment. FIG. 3 illustrates a perspective bottom view of the sanitizing head 106 shown in FIG. 2. FIG. 4 illustrates an axial cross-sectional view of the sanitizing head 106 through line 4-4 of FIG. 2. Referring to FIGS. 2-4, the sanitizing head 106 includes a housing 111, a UV lamp 140, and range light sources 130 (shown in FIG. 5). The UV lamp 140 and the range light sources 130 are mounted to the housing 111. The housing 111 includes at least a shroud 112 and a cover plate 154.

The shroud 112 extends from a proximal end 116 to a distal end 118. The shroud 112 has a port 120 at the proximal end 116 that couples to a hose 122. The shroud 112 is curved to define an interior chamber 156. The shroud 112 has an exposed perimeter edge 158 at a front 159 of the housing 111. The exposed perimeter edge 158 defines a front opening 160 of the housing 111 at the front 159. The UV lamp 140 is held within the interior chamber 156 and emits UV light that exits the interior chamber 156 through the front opening 160.

Air 150 is configured to be drawn into the sanitizing head 106 through one or more openings 152 (or simply an open chamber) of the housing 111. The air 150 is drawn into the sanitizing head 106, such as via a vacuum generator within the backpack assembly 104 (shown in FIG. 1). The air 150 is drawn into the shroud 112, and cools the UV lamp 140 as it passes over and around the UV lamp 140. The UV lamp 140 may represent an excimer lamp, a mercury lamp, or the like. The air 150 passes into the port 120 and into the hose 122, such as within an air tube within the hose 122. The air 150 not only cools the UV lamp 140, but also removes ozone, which may be generated by operation of the UV lamp 140, within the shroud 112. The air 150 may be drawn to an air filter, such as an activated carbon filter, within the backpack assembly 104. In at least one embodiment, the portable sanitizing system 100 may also include an alternative ozone mitigation system. As an example, the ozone mitigation system may be disposed in the shroud 112 or another portion of the system, and may include an inert gas bath, or a face inert gas system, such as in U.S. Pat. No. 10,232,954.

Referring to FIGS. 3 and 4, a bumper 153 may be secured to the exposed perimeter edge 158 of the shroud 112. The bumper 153 may be formed of a resilient material, such as rubber, another elastomeric material, open or closed cell foam, and/or the like. The bumper 153 protects the sanitizing head 106 from damage in case the sanitizing head 106 inadvertently contacts a surface. The bumper 153 also protects the surface from damage. The bumper 153 may be transparent or at least translucent to enable light transmission therethrough from the range light sources 130 (shown in FIG. 5).

Referring to FIG. 4, in particular, the housing 111 of the sanitizing head 106 may include a cover plate or lens 154 that extends at least partially across the front opening 160 (below the UV lamp 140 in the illustrated orientation). The cover plate 154 may be formed of glass, for example, and may be configured to filter UV light emitted by the UV lamp 140. In at least one embodiment, the cover plate 154 is or otherwise includes a far UV band pass filter that filters UV light emitted by the UV lamp 140 to allow wavelengths in the far UV band to pass through the cover plate 154 while blocking other wavelengths. For example, the far UV band pass filter may enable wavelengths between 200 nm and 230 nm to pass through the cover plate 154. In another embodiment, the cover plate 154 may be or include a UV-C band pass filter that allows wavelengths in the UV-C band to pass through the cover plate 154, such as wavelengths between 230 nm and 280 nm. The sanitizing head 106 may include a reflector 142 along an interior surface 162 that reflects the UV light towards the front opening 160. The cover plate 154 is coupled to the shroud 112 at or proximate to the exposed perimeter edge 158. A rim 157 (such as a 0.020" thick Titanium rim) may connect the cover plate 154 to the shroud 112. The rim 157 may distribute impact loads therethrough and/or therearound.

Figure 5:
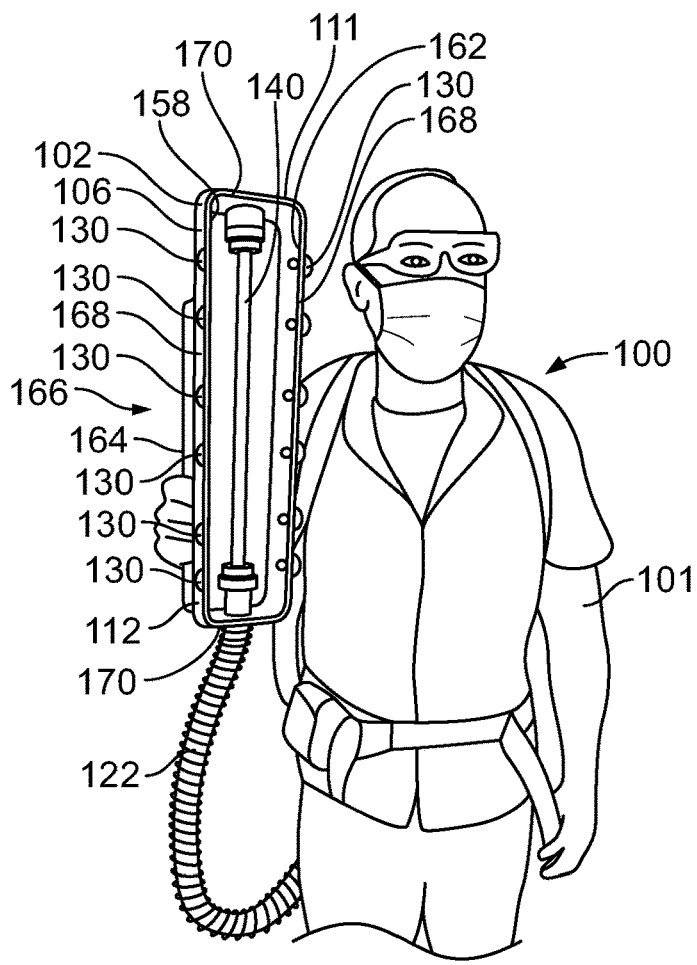
FIG. 5 depicts another embodiment of the portable sanitizing system of the present disclosure worn by an individual.

FIG. 5 depicts another embodiment of the portable sanitizing system 100 worn by an individual or user 101. In the illustrated embodiment, the wand assembly 102 lacks the handle 108 coupled to the sanitizing head 106 that is shown in FIG. 1. The sanitizing head 106 has a handle 164 that is an integral feature of the housing 111. For example, the handle 164 may be fixed to a rear 166 of the shroud 112. The other components of the portable sanitizing system 100 shown in FIG. 5 may be the same or similar to the embodiment shown in FIGS. 1-4. In FIG. 5, the cover plate 154 and the bumper 153 are omitted for descriptive purposes.

The range light sources 130 are disposed on the housing 111 and used to help the user 101 maintain a desired range to the target surface of the structure being sanitized. The range light sources 130 may be light emitting diodes (LEDs). In the illustrated embodiment, the range light sources 130 are mounted to the shroud 112 at or proximate to the exposed perimeter edge 158. For example, the range light sources 130 may contact the interior surface 162 of the shroud 112. Alternatively, the range light sources 130 may be mounted to other parts of the housing 111, such as the rim 157 and/or the cover plate 154.

The exposed perimeter edge 158 of the shroud 112 has multiple segments. In the illustrated embodiment, the edge 158 has a rectangular shape that includes two longer segments 168 and two shorter segments 170. The longer segments 168 have greater lengths than the shorter segments 170. The longer segments 168 extend along both sides of the UV lamp 140 such that the UV lamp 140 is between the two longer segments 168. A length axis of the UV lamp 140 is parallel to the longer segments 168. In the illustrated embodiment, the range light sources 130 are located on both of the longer segments 168 of the exposed perimeter edge 158 and are not located on the shorter segments 170. The multiple range light sources 130 are disposed on each longer segment 168 to define two parallel lines or rows 174 (shown in FIG. 6) of light sources 130. In one or more other embodiments, the range light sources 130 are also mounted to the shorter segments 170 and/or may be mounted at corners between the shorter and longer segments 168, 170.

Figure 6:
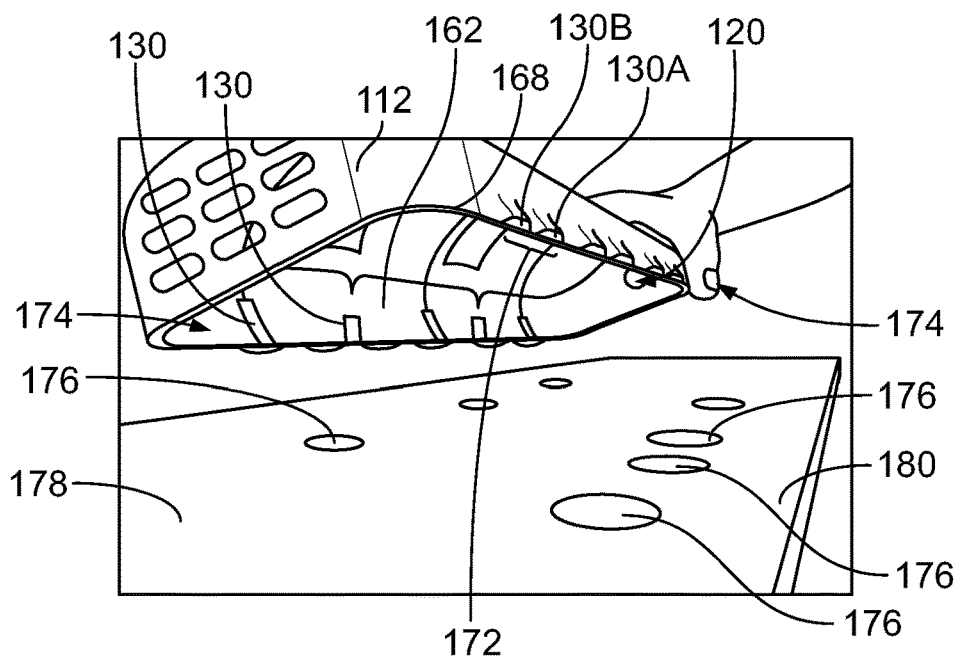
FIG. 6 is a front perspective view of a shroud and range light sources, according to an embodiment of the present disclosure.
Figure 7:
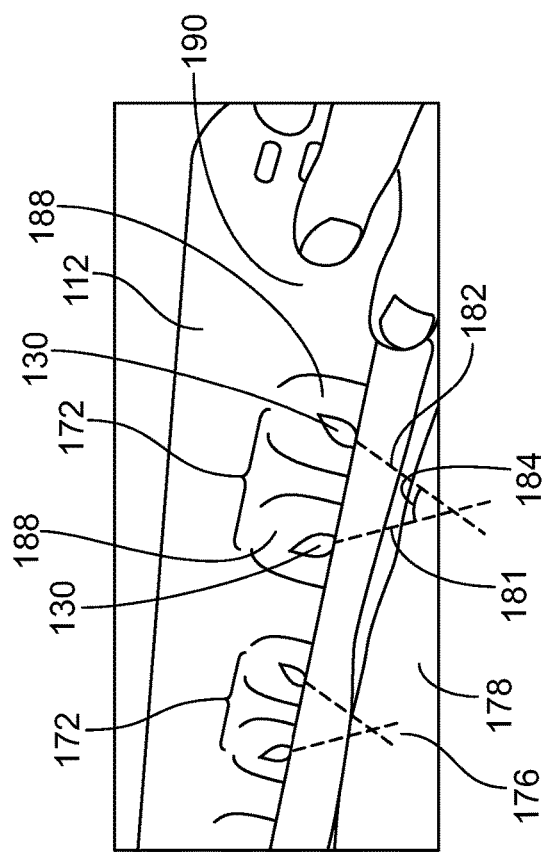
FIG. 7 is a side perspective view of a portion of the shroud and the range light sources shown in FIG. 6.

FIG. 6 is a front perspective view of the shroud 112 and the range light sources 130 according to an embodiment. FIG. 7 is a side perspective view of a portion of the shroud 112 and the range light sources 130 shown in FIG. 6. The shroud 112 may be at least partially translucent such that light emitted from the range light sources 130 located inside the shroud 112 is visible through the thickness of the shroud 112, as shown in FIGS. 6 and 7.

Referring to FIG. 6, the range light sources 130 are spaced apart from each other along the two parallel rows 174. The range light sources 130 may be light emitting diodes (LEDs). The conductive wires and other hardware may be routed along the interior surface 162 of the shroud 112 and exit through the port 120 into the hose 122 (shown in FIG. 5) to connect to an electrical power source, such as a battery in the backpack assembly 104 (shown in FIG. 1). The LEDs may be narrow divergence LEDs that limit the spread of the emitted light. The divergence of the LEDs may be no greater than 30 degrees, such as no greater than 20 degrees. In a non-limiting example, the divergence may be no greater than 10 degrees. Alternatively, the LEDs may not be narrow divergence LEDs. As shown in FIG. 6, each range light source 130 emits respective light or light beam forward of the shroud 112 that illuminates a nearby structure 180 to form a respective light marker 176 on the target surface 178 of the structure 180. The light markers 176 in FIG. 6 are approximately circular or ellipsoidal in shape.

Referring to FIG. 7, the range light sources 130 are arranged in one or more pairs 172. In the illustrated embodiment, there are multiple pairs 172, but only a single pair 172 of range light sources 130 may be utilized in a basic embodiment. The range light sources 130 in each pair 172 are oriented relative to each other to emit respective light beams that converge at a predetermined distance in front of the UV lamp 140 (shown in FIG. 5). For example, the two range light sources 130 in each pair 172 may be angled towards each other such that an aiming axis 181 of the first range light source 130 and an aiming axis 182 of the second range light source 130 in the pair 172 intersect at the predetermined distance. The light beams are emitted generally along the respective aiming axes 181, 182. The range light sources 130 in the pair 172 may be oriented relative to each other at an angle 184 (defined between the axes 181, 182) that is in a range between 10 degrees and 80 degrees. As described herein, ranges referred to as being "between" two end values are inclusive of the end values unless specifically addressed. The angle 184 may be between 20 degrees and 60 degrees. The angle 184 is determined based on the intended sanitizing application and the known characteristics of the UV light that is emitted. More specifically, the angle 184 is determined such that the convergence occurs at a designated distance in front of the UV lamp that corresponds to a desired proximity of the UV lamp to the target surface which yields effective disinfection.

The two range light sources 130 in each pair 172 may emit different colored light in order to visually distinguish between the light emitted from the different light sources 130. For example, the light marker 176 in FIG. 6 emitted by a first range light source 130A of a pair 172 may be a difference color than the light marker 176 emitted by a second range light source 130B of the pair 172. In an example, the first range light source 130A may emit blue or green light, and the second range light source 130B may emit amber, yellow, orange, or red light.

As shown in FIGS. 6 and 7, the two range light sources 130 in each pair 172 are adjacent to each other and located on a common segment 168 of the shroud 112. The two light sources 130 in each pair 172 may be separated by a discrete spacing distance, such as 1 inch, 2 inches, 3 inches, 4 inches, or the like. The spacing distance also affects the relative angle 184 at which the light sources 130 are oriented in order to provide converging light at a designated distance in front of the UV lamp 140. In the illustrated embodiment, the shroud 112 includes three discrete pair 172 of range light sources 130 on each of the two longer segments 168, for a total of twelve range light sources 130. The number and arrangement of the range light sources 130 may be based on the dimensions of the shroud 112 such that more or fewer light sources 130 can be used in other embodiments. Optionally, the shroud 112 may include molded bulges 188 along an exterior surface 189 of the shroud 112 at the locations of the range light sources 130. The bulges 188 protrude outward to provide individual spaces for the range light sources 130 within the shroud 112.

Figure 8:
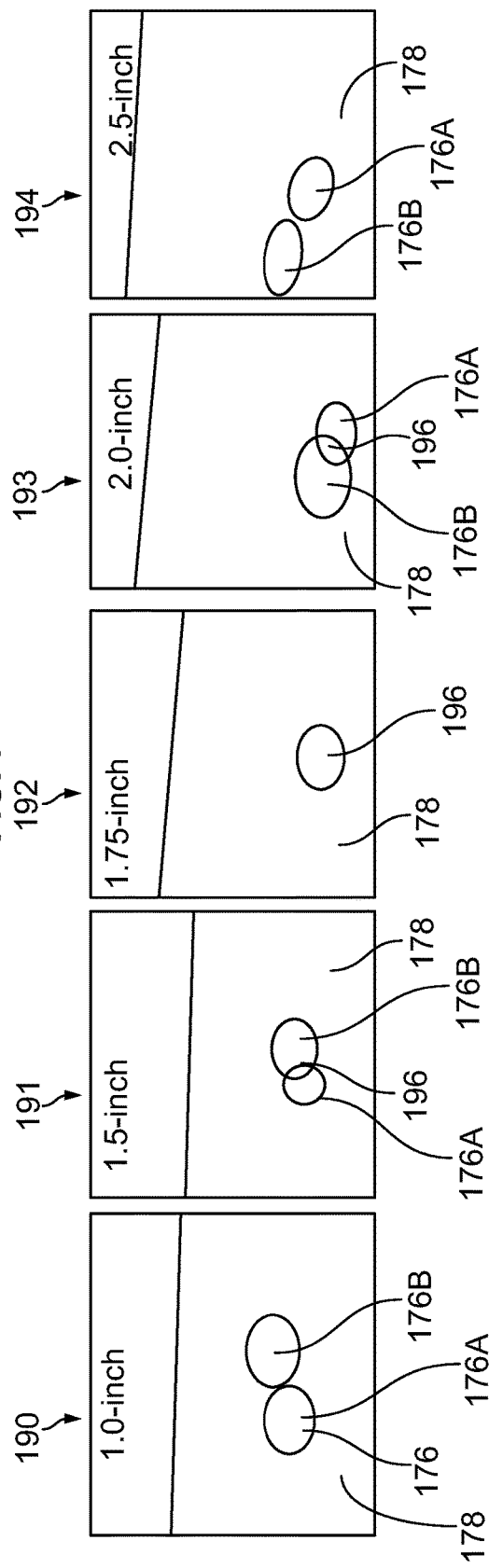
FIG. 8 depicts five images showing light markers emitted by a pair of range light sources from different distances relative to a target surface, according to an embodiment of the present disclosure.

FIG. 8 depicts five images 190-194 showing the light markers 176 emitted by a pair 172 of range light sources 130 from different distances relative to a target surface 178. FIG. 8 shows how the relative positioning of the light markers 176 can provide guidance to a user concerning whether the sanitizing head 106 is located at a desired distance from the target surface 178 to provide effective disinfection. For example, the first image 190 shows the light markers 176 at a distance of 1.0 inch from the surface 178. The second image 191 shows the light markers 176 at a distance of 1.5 inches from the surface 178. The third image 192 shows the light markers 176 at a distance of 1.75 inches from the surface 178. The fourth image 193 shows the light markers 176 at a distance of 2.0 inches from the surface 178, and the fifth image 194 shows the light markers 176 at a distance of 2.5 inches from the surface 178. The distances may be refer to the distance between the UV lamp 140 and the area of the target surface 178 that is illuminated by the UV light emitted by the UV lamp 140. The light markers 176 include a first light marker 176A and a second light marker 176B that have different colors and are emitted by different range light sources 130 in a single pair 172. For example, the first light marker 176A may be amber, and the second light marker 176B may be blue.

In the illustrated embodiment, the two range light sources 130 in the pair 172 are intentionally oriented for the light beams emitted from the light sources to converge at a distance of 1.75 inches. That convergence distance may be determined based on characteristics of the UV light and/or disinfecting properties. For example, that convergence distance may represent a distance in which the UV light provides desirable sanitization to kill or neutralize pathogens. When the sanitizing head 106 is held too close to the target surface 178, such as at 1.0 inches as shown in image 190, the first and second markers 176A, 176B are generally discrete with little or no overlap. The lack of overlap is visible to the user which indicates that the sanitizing head 106 is not in correct position. The user moves the sanitizing head 106 closer or farther from the surface 178 to cause the markers 176A, 176B to move together. In this case, moving the sanitizing head 106 farther away to 1.5 inches as shown in image 191 causes the markers 176A, 176B to partially converge and define an overlap region 196. The overlap region 196 is the area that is concurrently illuminated by both of the range image sources 130 in the pair 172. The overlap region 196 may have a different color than the individual markers 176A, 176B, such as a lighter or whiter color. As the sanitizing head 106 is moved even farther away from the surface 178, the size of the overlap region 196 increases until the distance reaches 1.75 inches as shown in image 192. In image 192, the two markers 176A, 176B almost completely overlap such that there is essentially only one light marker now instead of two. This large overlap region 196 (e.g., and the singular marker) indicate to the user that the sanitizing head 106 is positioned at a desirable height or distance from the target surface 178 to provide effective disinfecting.

Additional movement of the sanitizing head 106 away from the target surface 178 causes the overlap region 196 to shrink as the discrete amber and blue light markers 176A, 176B become visible and move apart from each other, which is shown in images 193 and 194. Although the visual cues shown in images 190 and 194 look similar, the user can quickly determine if the sanitizing head 106 should be moved closer or farther from the target surface 178 to achieve the desired positioning by moving the sanitizing head 106 closer or farther from the surface 178 and observing whether the individual markers 176A, 176B move closer together or farther away. If the markers 176A, 176B diverge even more, then that indicates that the sanitizing head 106 should be moved in the opposite direction.

Figure 9:
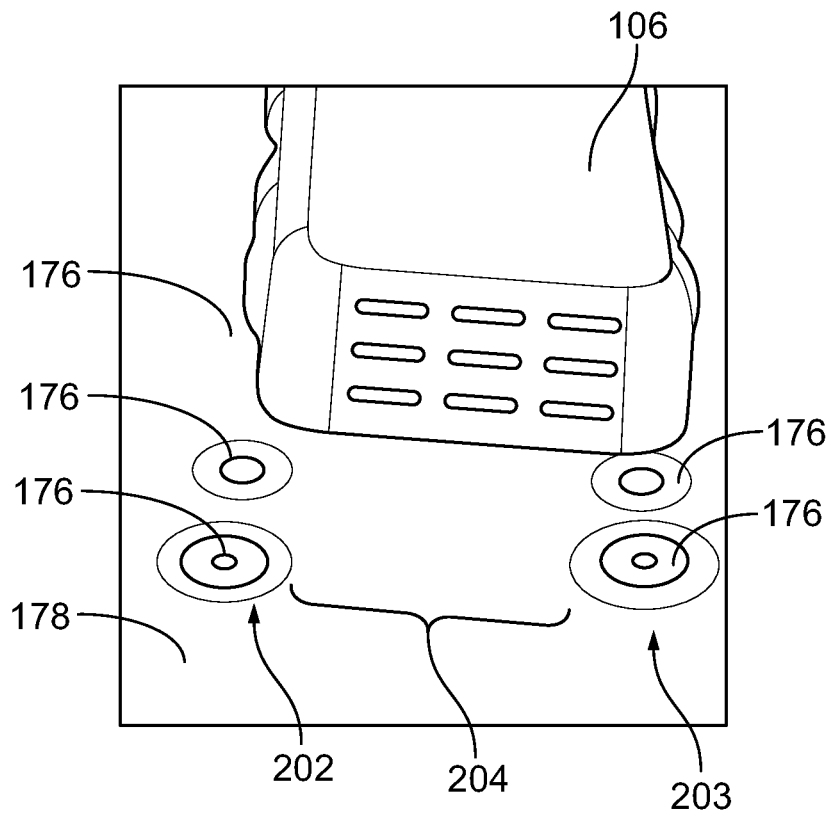
FIG. 9 is an end view of the sanitizing head showing the light markers on the target surface that is being sanitized, according to an embodiment of the present disclosure.
Figure 10:
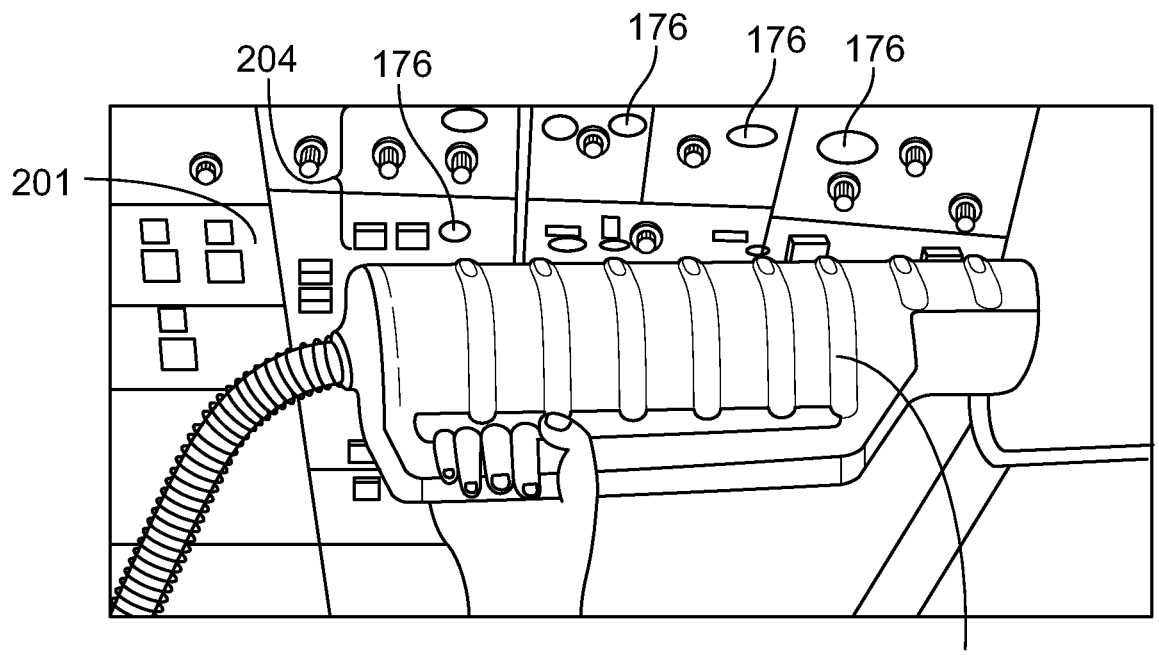
FIG. 10 is a side perspective view showing the sanitizing head used to sanitize and disinfect an instrument panel, according to an embodiment of the present disclosure.

FIG. 9 is an end view of the sanitizing head 106 showing the light markers 176 on the target surface 178 that is being sanitized. FIG. 10 is a side perspective view showing the sanitizing head 106 used to sanitize and disinfect an instrument panel 201. The light markers 176 illuminate the target surface 178 in two parallel rows 202, 203. The two rows 202, 203 can provide a visual indication to the user of the area that is being disinfected. For example, the intervening area 204 between the two rows 202, 203 is illuminated with UV light from the UV lamp 140. In addition to provided range guidance in the depth dimension, by bordering or framing the UV illuminated area 204, the range light sources 130 help the user determine which section of the target surface 178 is receiving a dose of UV radiation (e.g., is being disinfected) at any given time. The user may not be able to see the UV light itself.

Figure 11:
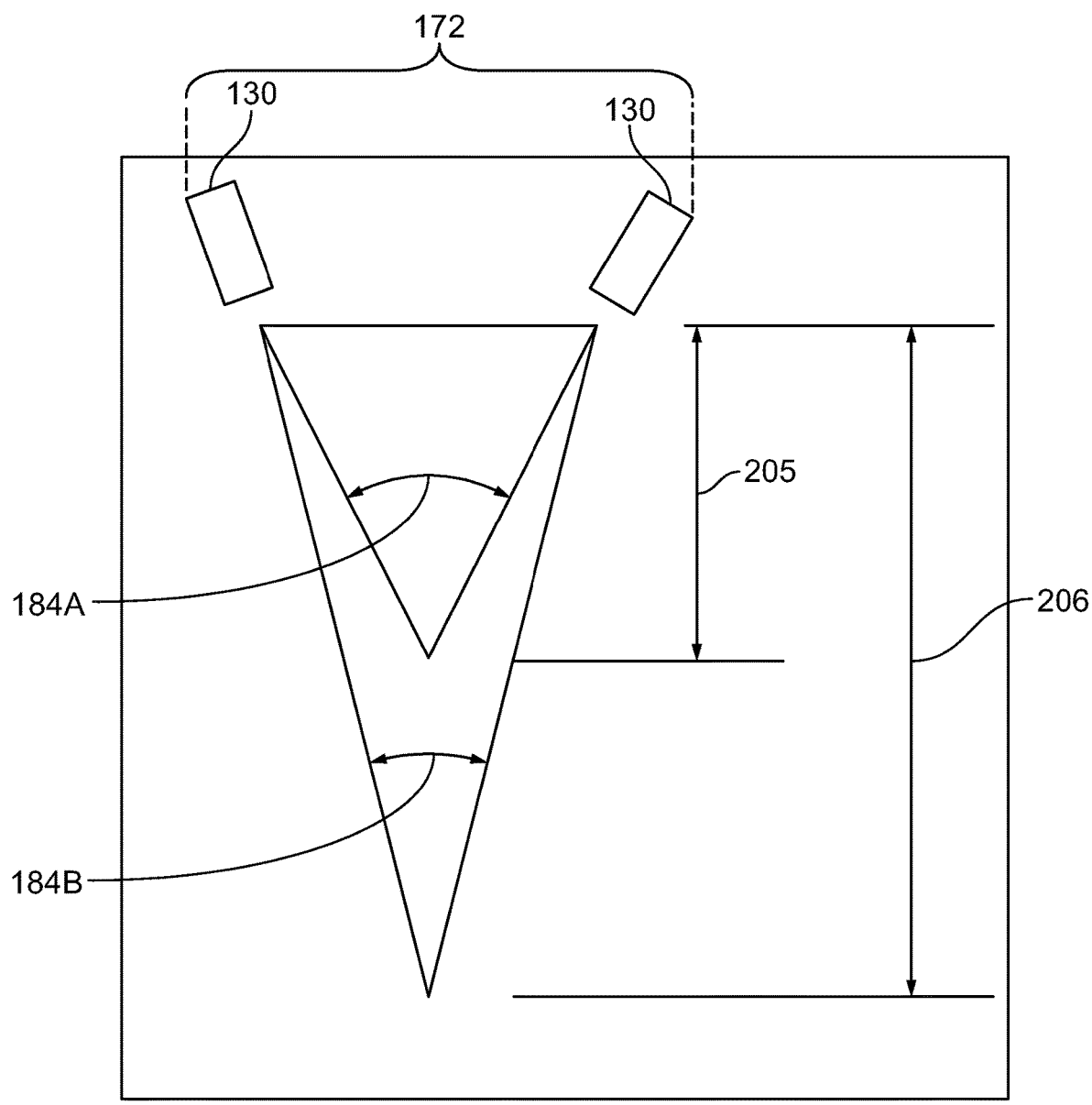
FIG. 11 is a diagram showing multiple relative angles between two range light sources in a pair, according to an embodiment of the present disclosure.

FIG. 11 is a diagram showing multiple relative angles between the two range light sources 130 in a pair 172 according to an embodiment. The LEDs used for the range light sources 130 may have a narrow divergence of 8 to 10 degrees. The relative angle 184A, 184B in the housing 111 is predetermined based on the type of UV lamp 140 used and the intended use of the disinfecting system. For example, when disinfecting flat surfaces, such as a cabin area within a vehicle, a desirable distance between the UV lamp 140 and the target surface may be between 1 and 3 inches, inclusive of the end points. In an embodiment, the desirable distance may be approximately 2 inches. Based on a predetermined separation distance between each other, the range light sources 130 in the pair 172 may be set at an angle of approximately 53 degrees from one another. At this angle, the light beams emitted from the two light sources 130 will converge at a distance in front of the sanitizing head 106 that matches the desired distance, such as 2 inches. Therefore, when the markers converge at the overlap region as shown in image 192 of FIG. 8, that indicates to the user that the sanitizing head 106 is at the correct distance 205 from the target surface for the intended application.

When disinfecting surfaces with protrusions, such as a flight deck of an aircraft, a desirable distance between the UV lamp 140 and the target surface may be between 3 and 6 inches, inclusive of the end points. The desirable distance 206 may be approximately 4 inches (e.g., within 5%, 10%, or 15% of 4.0 inches). At the same predetermined separation distance, the range light sources 130 in the pair 172 may be set at an angle of approximately 28 degrees from one another. At this angle, the light beams emitted from the two light sources 130 will converge at a distance in front of the sanitizing head 106 that matches the desired distance, such as 4 inches. Therefore, when the markers converge at the overlap region as shown in image 192 of FIG. 8, that indicates to the user that the sanitizing head 106 is at the correct distance 206 from the target surface for the intended application.

Figure 12:
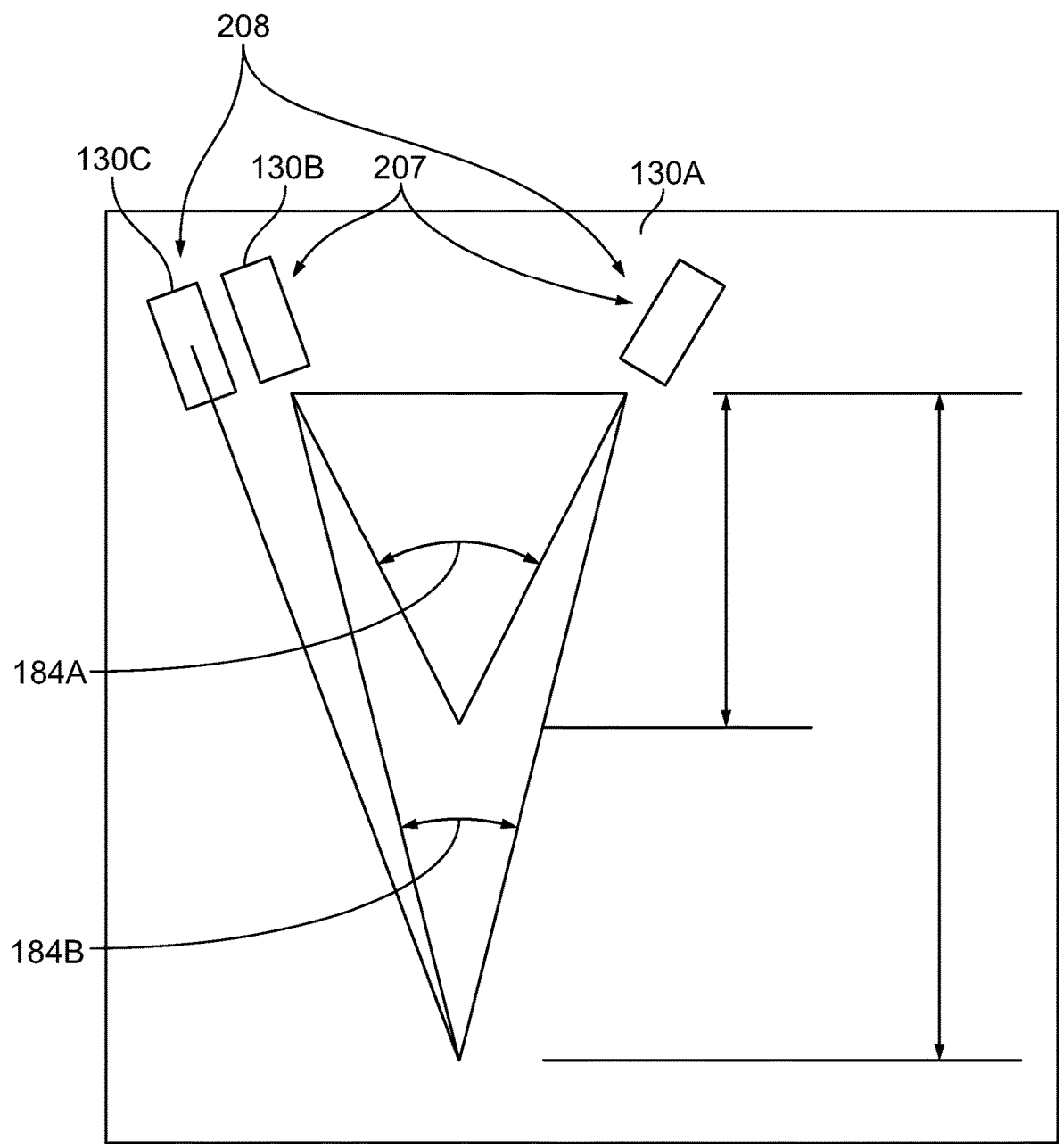
FIG. 12 is a diagram showing three range light sources, according to an alternative embodiment of the present disclosure.

FIG. 12 is a diagram showing three range light sources 130 according to an alternative embodiment. The sanitizing head 106 may include at least one pair of range light sources 130 arranged in a first subset 207 and at least one pair of range light sources 130 arranged in a second subset 208. Each of the subsets 207, 208 may include one pair or multiple pairs of range light sources 130. The pairs in the first subset 207 are oriented at a different relative angle than the pairs in the second subset 208. For example, the pairs in the first subset 207 may have a first relative angle 184A that is greater than a second relative angle 184B of the pairs in the second subset 208. The first relative angle 184A may be at least 40 degrees and no greater than 60 degrees. In a non-limiting example, the first relative angle 184A is approximately 53 degrees. The second relative angle 184B may be no less than 20 degrees and less than 40 degrees. In a non-limiting example, the second relative angle 184B is approximately 28 degrees. The range light sources 130 may be selectively controlled via the user or an automated control system to individually operate the first and second subsets 207, 208. For example, the first subset 207 can be operated without the second subset 208 for a first intended application, and the second subset 208 can be operated without the first subset 207 for a second intended application. The first intended application could be to clean a cabin area within a vehicle, and the second intended application could be to clean a flight deck of an aircraft.

Optionally, at least one range light source 130 can define part of two different pairs. For example, the illustrated diagram shows a first range light source 130A, a second range light source 130B, and a third range light source 130C. The second and third range light sources 130B, 130C may emit the same colored light, such as blue light. The first range light source 130A defines a pair in the first subset 207 with the second range light source 130B. The first range light source 130A defines a pair in the second subset 208 with the third range light source 130C. The third range light source 130C represents one of an alternate set of LEDs along one side of the housing 111. The second and third range light sources 130B, 130C are disposed on the same side of the housing 111 but set at different angles to allow the user to switch the optimum disinfecting distance based on the intended use. A switch can be installed to change the focus from 2 inches to 4 inches depending upon the desired range (switching from blue LED1 to blue LED2) without changing the red LED 130A.

Figure 13:
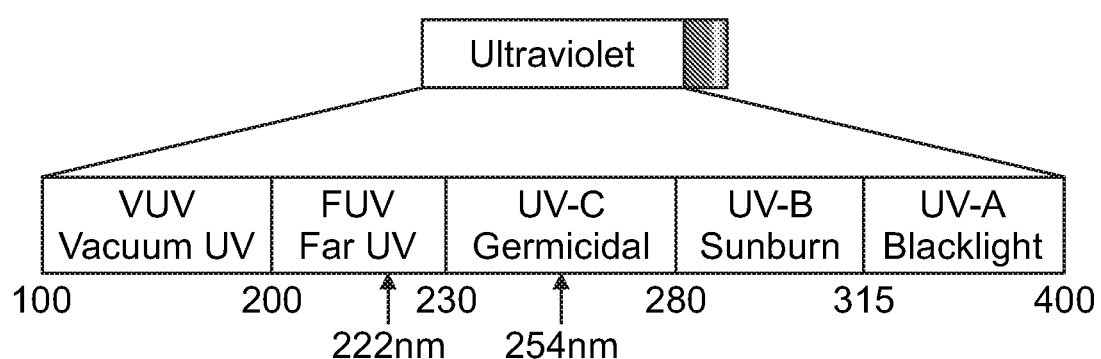
FIG. 13 illustrates an ultraviolet light spectrum, according to an embodiment of the present disclosure.

FIG. 13 illustrates an ultraviolet light spectrum. In an embodiment, the sanitizing head 106 may be configured to emit sanitizing UV light (through operation of the UV lamp 140) within a far UV spectrum, such as between 200 nm and 230 nm. For example, the sanitizing head 106 may emit sanitizing UV light having a wavelength of approximately 222 nm. In another embodiment, the sanitizing head 106 may be configured to emit sanitizing UV light (through operation of the UV lamp 140) within a UV-C spectrum, such as between 230 nm and 280 nm. For example, the sanitizing head 106 may emit sanitizing UV light having a wavelength of approximately 254 nm.

Figure 14:
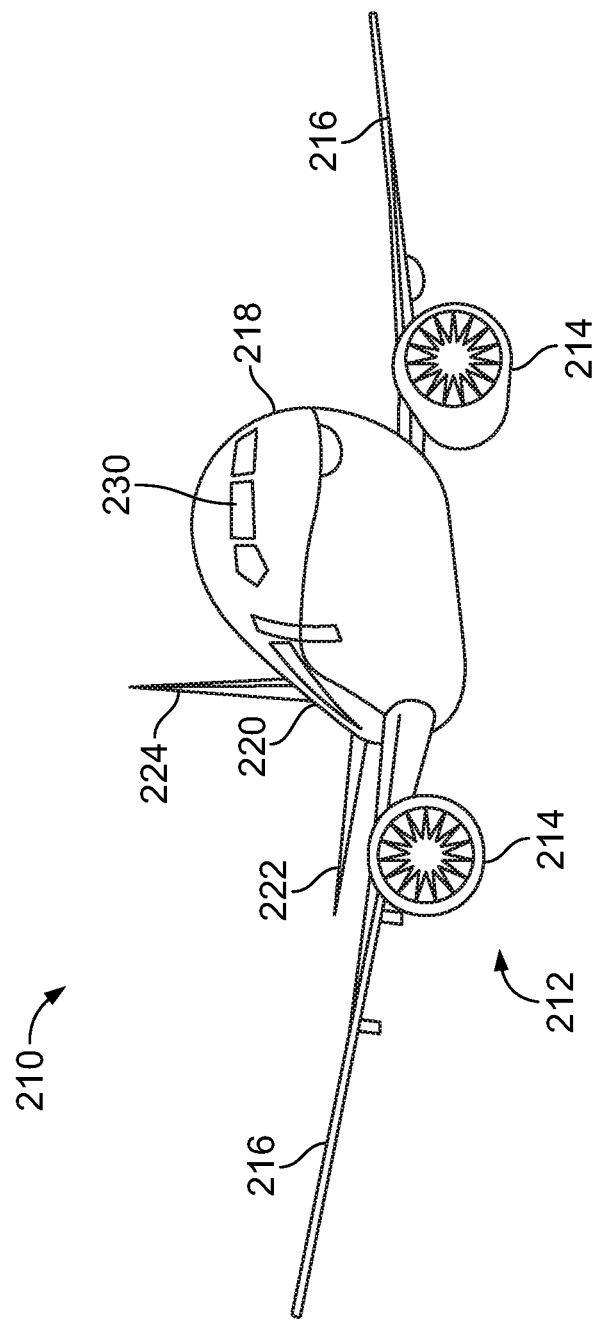
FIG. 14 illustrates a perspective front view of an aircraft, according to an embodiment of the present disclosure.

FIG. 14 illustrates a perspective front view of an aircraft 210, according to an embodiment of the present disclosure. The aircraft 210 includes a propulsion system 212 that includes engines 214, for example. Optionally, the propulsion system 212 may include more engines 214 than shown. The engines 214 are carried by wings 216 of the aircraft 210. In other embodiments, the engines 214 may be carried by a fuselage 218 and/or an empennage 220. The empennage 220 may also support horizontal stabilizers 222 and a vertical stabilizer 224.

The fuselage 218 of the aircraft 210 defines an internal cabin 230, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 230 includes one or more lavatory systems, lavatory units, or lavatories, as described herein.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 15A:
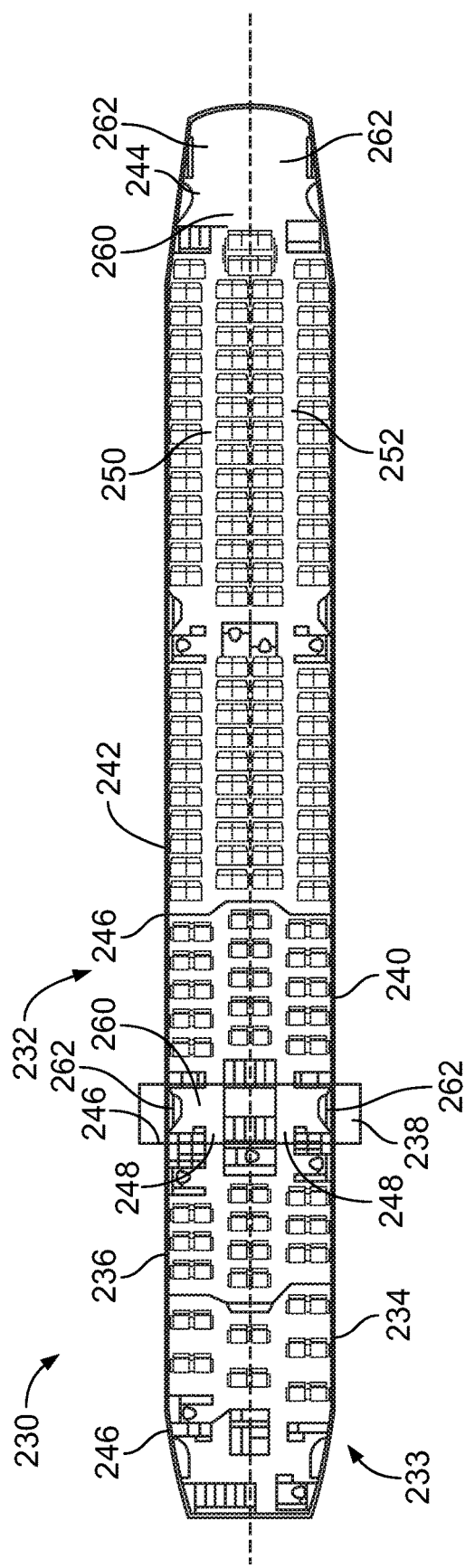
FIG. 15A illustrates a top plan view of an internal cabin of an aircraft, according to an embodiment of the present disclosure.

FIG. 15A illustrates a top plan view of an internal cabin 230 of an aircraft, according to an embodiment of the present disclosure. The internal cabin 230 may be within the fuselage 232 of the aircraft, such as the fuselage 218 of FIG. 14. For example, one or more fuselage walls may define the internal cabin 230. The internal cabin 230 includes multiple sections, including a front section 233, a first class section 234, a business class section 236, a front galley station 238, an expanded economy or coach section 240, a standard economy of coach section 242, and an aft section 244, which may include multiple lavatories and galley stations. It is to be understood that the internal cabin 230 may include more or less sections than shown. For example, the internal cabin 230 may not include a first class section, and may include more or less galley stations than shown. Each of the sections may be separated by a cabin transition area 246, which may include class divider assemblies between aisles 248.

As shown in FIG. 15A, the internal cabin 230 includes two aisles 250 and 252 that lead to the aft section 244. Optionally, the internal cabin 230 may have less or more aisles than shown. For example, the internal cabin 230 may include a single aisle that extends through the center of the internal cabin 230 that leads to the aft section 244.

The aisles 248, 250, and 252 extend to egress paths or door passageways 260. Exit doors 262 are located at ends of the egress paths 260. The egress paths 260 may be perpendicular to the aisles 248, 250, and 252. The internal cabin 230 may include more egress paths 260 at different locations than shown. The portable sanitizing system 100 shown and described with respect to FIGS. 1-13 may be used to sanitize various structures within the internal cabin 230, such as passenger seats, monuments, stowage bin assemblies, components on and within lavatories, galley equipment and components, and/or the like.

Figure 15B:
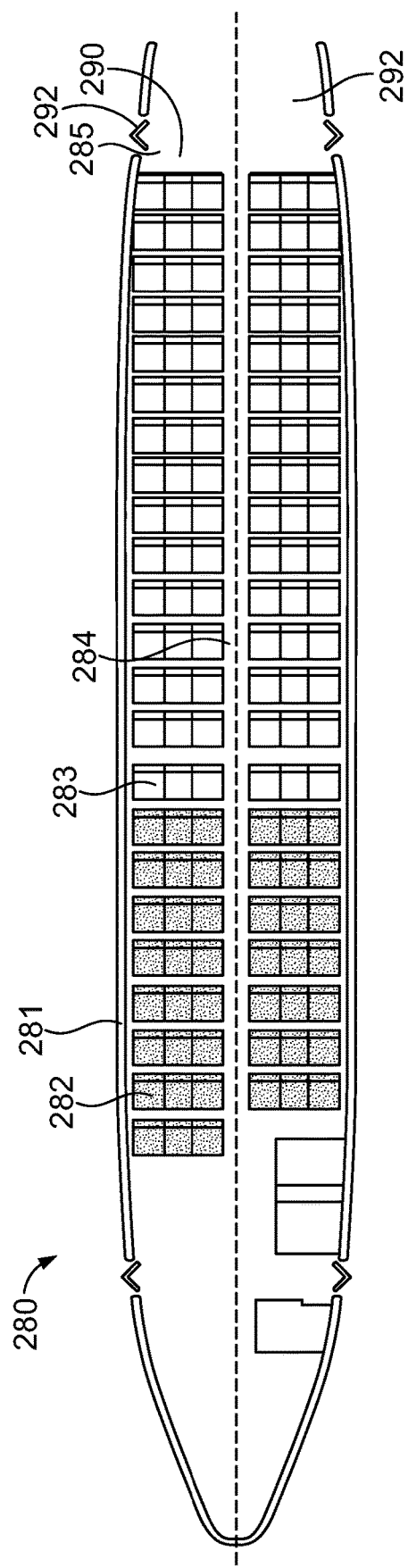
FIG. 15B illustrates a top plan view of an internal cabin of an aircraft, according to an embodiment of the present disclosure.

FIG. 15B illustrates a top plan view of an internal cabin 280 of an aircraft, according to an embodiment of the present disclosure. The internal cabin 280 is an example of the internal cabin 230 shown in FIG. 14. The internal cabin 280 may be within a fuselage 281 of the aircraft. For example, one or more fuselage walls may define the internal cabin 280. The internal cabin 280 includes multiple sections, including a main cabin 282 having passenger seats 283, and an aft section 285 behind the main cabin 282. It is to be understood that the internal cabin 280 may include more or less sections than shown.

The internal cabin 280 may include a single aisle 284 that leads to the aft section 285. The single aisle 284 may extend through the center of the internal cabin 280 that leads to the aft section 285. For example, the single aisle 284 may be coaxially aligned with a central longitudinal plane of the internal cabin 280.

The aisle 284 extends to an egress path or door passageway 290. Exit doors 292 are located at ends of the egress path 290. The egress path 290 may be perpendicular to the aisle 284. The internal cabin 280 may include more egress paths than shown. The portable sanitizing system 100 shown and described with respect to FIGS. 1-13 may be used to sanitize various structures within the internal cabin 230, such as passenger seats, monuments, stowage bin assemblies, components on and within lavatories, galley equipment and components, and/or the like.

Figure 16:
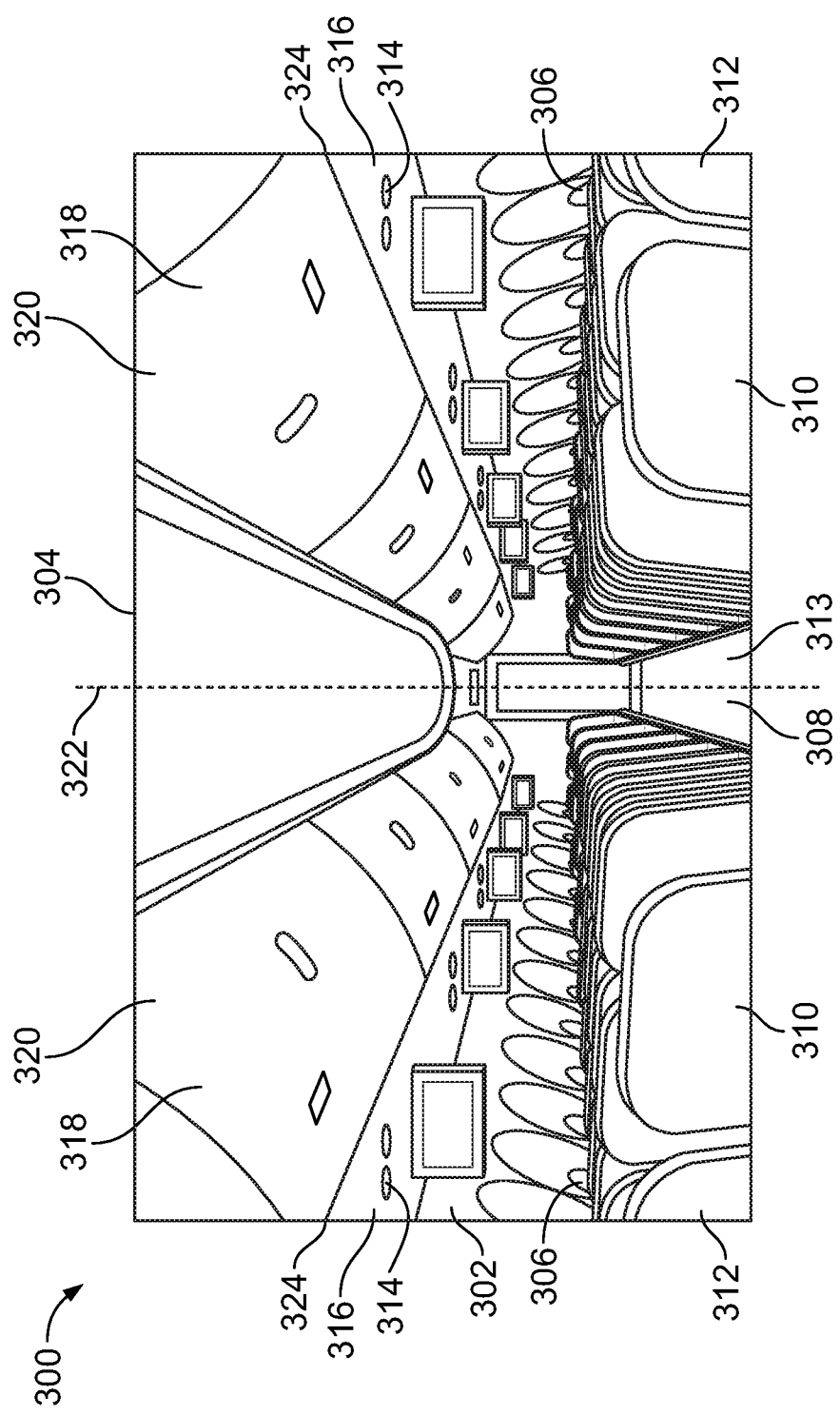
FIG. 16 illustrates a perspective interior view of an internal cabin of an aircraft, according to an embodiment of the present disclosure.

FIG. 16 illustrates a perspective interior view of an internal cabin 300 of an aircraft, according to an embodiment of the present disclosure. The internal cabin 300 includes outboard walls 302 connected to a ceiling 304. Windows 306 may be formed within the outboard walls 302. A floor 308 supports rows of seats 310. As shown in FIG. 16, a row 312 may include two seats 310 on either side of an aisle 313. However, the row 312 may include more or less seats 310 than shown. Additionally, the internal cabin 300 may include more aisles than shown.

Passenger service units (PSUs) 314 are secured between an outboard wall 302 and the ceiling 304 on either side of the aisle 313. The PSUs 314 extend between a front end and rear end of the internal cabin 300. For example, a PSU 314 may be positioned over each seat 310 within a row 312. Each PSU 314 may include a housing 316 that generally contains vents, reading lights, an oxygen bag drop panel, an attendant request button, and other such controls over each seat 310 (or groups of seats) within a row 312.

Overhead stowage bin assemblies 318 are secured to the ceiling 304 and/or the outboard wall 302 above and inboard from the PSU 314 on either side of the aisle 313. The overhead stowage bin assemblies 318 are secured over the seats 310. The overhead stowage bin assemblies 318 extend between the front and rear end of the internal cabin 300. Each stowage bin assembly 318 may include a pivot bin or bucket 320 pivotally secured to a strongback (hidden from view in FIG. 16). The overhead stowage bin assemblies 318 may be positioned above and inboard from lower surfaces of the PSUs 314. The overhead stowage bin assemblies 318 are configured to be pivoted open in order to receive passenger carry-on baggage and personal items, for example.

As used herein, the term "outboard" means a position that is further away from a central longitudinal plane 322 of the internal cabin 300 as compared to another component. The term "inboard" means a position that is closer to the central longitudinal plane 322 of the internal cabin 300 as compared to another component. For example, a lower surface of a PSU 314 may be outboard in relation to a stowage bin assembly 318.

The portable sanitizing system 100 shown and described with respect to FIGS. 1-13 may be used to sanitize various structures shown within the internal cabin 300. Appendix B shows the portable sanitizing system 100 being used to sanitize various components within a cockpit or flight deck of an aircraft.

When not in use, the portable sanitizing system 100 may be stored within a closet, galley cart bay, or galley cart, such as within the internal cabin of the vehicle.

Figure 17:
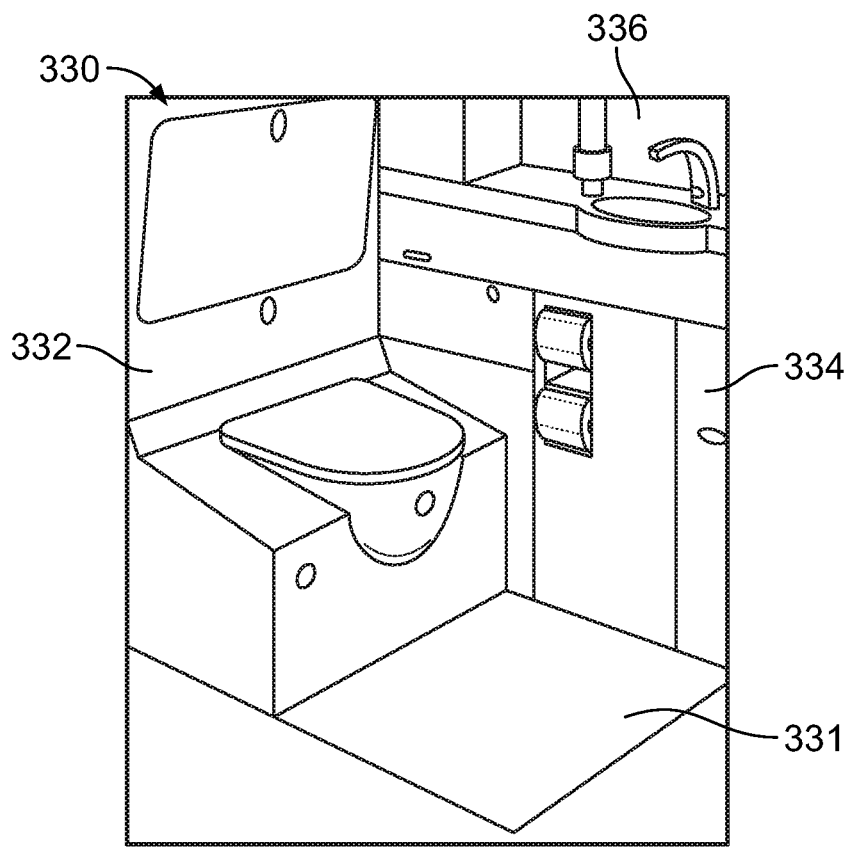
FIG. 17 illustrates a perspective internal view of a lavatory within an internal cabin of a vehicle, according to an embodiment of the present disclosure.

FIG. 17 illustrates a perspective internal view of a lavatory 330 within an internal cabin of a vehicle, such as any of the internal cabins described herein. The lavatory 330 is an example of an enclosed space, monument, or chamber, such as within the internal cabin a vehicle. The lavatory 330 may be onboard an aircraft, as described above. Optionally, the lavatory 330 may be onboard various other vehicles. In other embodiments, the lavatory 330 may be within a fixed structure, such as a commercial or residential building. The lavatory 330 includes a base floor 331 that supports a toilet 332, cabinets 334, and a sink 336 or wash basin. The lavatory 330 may be arranged differently than shown. The lavatory 330 may include more or less components than shown. The portable sanitizing system 100 shown and described with respect to FIGS. 1-13 may be used to sanitize the various structures, components, and surfaces within the lavatory 330.

Figure 18:
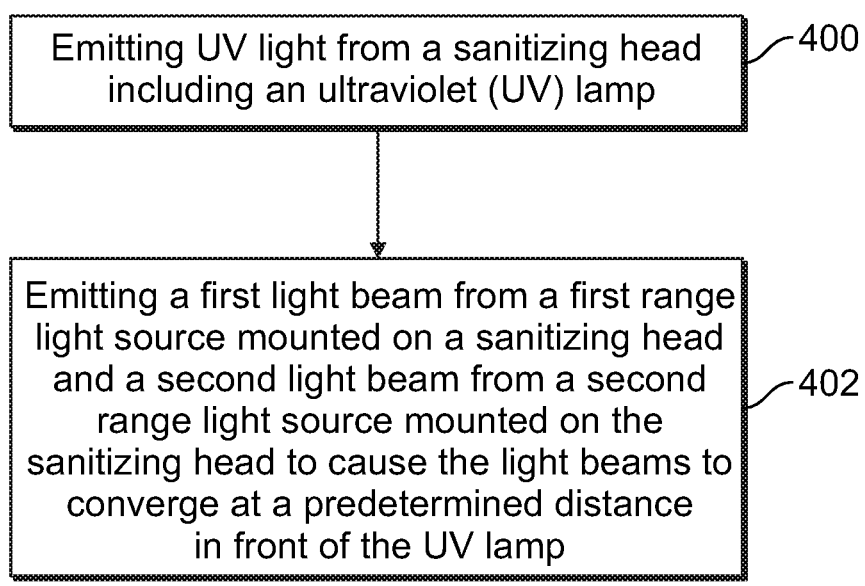
FIG. 18 illustrates a flow chart of a portable sanitizing method, according to an embodiment of the present disclosure.

FIG. 18 illustrates a flow chart of a portable sanitizing method, according to an embodiment of the present disclosure. The method includes emitting (400) UV light from a sanitizing head 106 that includes an ultraviolet (UV) lamp 140. The method also includes emitting (402) a first light beam from a first range light source 130A mounted on the sanitizing head 106 and a second light beam from a second range light source 130B mounted on the sanitizing head 106. The first and second range light sources 130A, 130B are arranged in a pair 172 and oriented relative to each other such that the respective light beams converge at a predetermined distance in front of the UV lamp 140.

Referring to FIGS. 1-13, the portable sanitizing system 100 can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing system 100 is used to augment or modify a cleaning process, such as to augment manual cleaning or to replace manual cleaning.

The pairs of range light sources provide range guidance to the user manipulating the portable sanitizing head by providing visual feedback that indicates whether the sanitizing head is too close to, too far from, or at a desired distance from the target surface of the structure that is being disinfected. For example, each pair of different colored LED lights (e.g., amber and blue) converge into one light marker to indicate the sanitizing head is at a desired distance from the target surface. The range lights also visually indicate the edges of the area that is cleaned by the UV light because the UV light itself may be difficult to visualize.

In a non-limiting embodiment, the range light sources may be arranged in two rows with the UV lamp disposed between the two rows. Optionally, the LED range lights are narrow field of view LEDs positioned along both sides of the length of the housing at an exposed perimeter edge at the front of the housing. The two range light sources in each pair may be disposed adjacent each other in the same row and spaced apart by a designated spacing, such as two inches.

The form factor of the portable sanitizing system can vary for different applications. For example, the system can include a backpack assembly that is coupled to the sanitizing head (or wand) via a hose. In another example, the system can include a carrying case that is coupled to the sanitizing head via a hose. The carrying case may be smaller than the backpack assembly and may lack shoulder straps. For example, the carrying case may have a handle for carrying the case by hand. In another example, the system can include a wheeled case that is coupled to the sanitizing head via a hose. In still another example, the hose can be relatively long and coupled to a fixed structure, such as a stationary power source mounted in a vehicle or in a building. The sanitizing head is portable, while tethered to the power source via the hose, to sanitizing the internal cabin of the vehicle or building. For each of the described examples, the hose can be used to supply to or draw air across the UV lamp at the sanitizing head, and may also be used to power the UV lamp and the range light sources.

As described herein, embodiments of the present disclosure provide systems and a methods for efficiently sterilizing surfaces, components, structures, and/or the like within an internal cabin of a vehicle. Further, embodiments of the present disclosure provide compact, easy-to-use, and safe systems and methods for using UV light to sterilize surfaces within an internal cabin.

Clause 1: A sanitizing head comprises a housing and multiple range light sources. The housing retains an ultraviolet (UV) lamp. UV light emitted from the UV lamp exits through a front end of the housing. The range light sources are secured to the housing and arranged in one or more pairs. The range light sources in each pair of the one or more pairs are oriented relative to each other to emit respective light beams that converge at a predetermined distance in front of the UV lamp.

Clause 2: The sanitizing head of Clause 1, wherein the housing includes a shroud that defines a front opening, and the range light sources are spaced apart along an exposed perimeter edge of the shroud at the front opening.

Clause 3: The sanitizing head of Clause 2, wherein the exposed perimeter edge is rectangular and includes two longer segments that extend between two shorter segments. The range light sources are disposed on the two longer segments.

Clause 4: The sanitizing head of Clause 2, wherein the exposed perimeter edge includes multiple segments, and the range light sources in each respective pair of the one or more pairs are disposed on a common segment of the multiple segments.

Clause 5: The sanitizing head of any of Clauses 1-4, wherein the light beams emitted by the range light sources in each pair have different colors.

Clause 6: The sanitizing head of any of Clauses 1-5, wherein the range light sources are light emitting diodes (LEDs) that have a divergence no greater than 10 degrees.

Clause 7: The sanitizing head of any of Clauses 1-6, wherein the range light sources in each pair are oriented at an angle in a range between 20 degrees and 60 degrees relative to each other.

Clause 8: The sanitizing head of any of Clauses 1-7, wherein the one or more pairs includes multiple pairs arranged in a first subset of one or more pairs and a second subset of one or more pairs. The range light sources in each pair within the first subset are oriented at a first relative angle and the range light sources in each pair within the second subset are oriented at a second relative angle that is different from the first relative angle.

Clause 9: The sanitizing head of Clause 8, wherein the first relative angle is at least 40 degrees and no greater than 60 degrees, and the second relative angle is at least 20 degrees and less than 40 degrees.

Clause 10: The sanitizing head of Clause 9, wherein the first relative angle is approximately 53 degrees, and the second relative angle is approximately 28 degrees.

Clause 11: The sanitizing head of any of Clauses 1-10, wherein the predetermined distance is no less than 1 inch and no greater than 6 inches.

Clause 12: The sanitizing head of any of Clauses 1-11, wherein the UV lamp is configured to emit UV light having a wavelength between 200 nm and 280 nm.

Clause 13: The sanitizing head of Clause 12, wherein the UV lamp is configured to emit UV light having a wavelength of approximately 222 nm.

Clause 14: The sanitizing head of Clause 12, wherein the UV lamp is configured to emit UV light having a wavelength of approximately 254 nm.

Clause 15: A portable sanitizing method comprises emitting ultraviolet (UV) light from a sanitizing head including a housing and a UV lamp. The method also includes emitting a first light beam from a first range light source on the sanitizing head and a second light beam from a second range light source on the sanitizing head to cause the first and second light beams to converge at a predetermined distance from the UV lamp.

Clause 16: The portable sanitizing method of Clause 15, wherein the first light beam and the second light beam have different colors.

Clause 17: The portable sanitizing method of either of Clauses 15 or 16, further comprising mounting the first and second range light sources at a relative angle on the housing to cause the first and second light beams to converge at a predetermined distance that is no less than 1 inch and no greater than 6 inches from the UV lamp.

Clause 18: The portable sanitizing method of any of Clauses 15-17, further comprising mounting multiple pairs of the range light sources along a housing of the sanitizing head in two parallel rows with the UV lamp disposed between the two parallel rows.

Clause 19: The portable sanitizing method of any of Clauses 15-18, wherein the first and second range light sources represent a pair within a first subset of one or more pairs of range light sources. The method further comprises deactivating the first subset and activating a second subset of one or more pairs of the range light sources. The one or more pairs in the second subset have a different relative angle between the range light sources than the one or more pairs in the first subset.

Clause 20: A sanitizing head comprising a housing an multiple range light sources. The housing retains an ultraviolet (UV) lamp configured to emit UV light. The housing includes a shroud that defines a front opening. The range light sources are secured to the housing and spaced apart along an exposed perimeter edge of the shroud at the front opening. The range light sources are arranged in one or more pairs. The range light sources in each pair are oriented relative to each other to emit respective light beams that converge at a predetermined distance in front of the UV lamp. The range light sources are light emitting diodes (LEDs) that have a divergence no greater than 10 degrees. The light beams emitted by the range light sources in each pair have different colors.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

As used herein, value modifiers such as "about" and "approximately" inserted before a numerical value indicate that the value can represent other values within a designated threshold range above and/or below the specified value, such as values within 5%, 10%, or 15% of the specified value.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing head comprising:
a housing that retains an ultraviolet (UV) lamp; and
multiple range light sources secured to the housing and arranged in one or more pairs, wherein the range light sources emit visible light, the range light sources in each pair of the one or more pairs oriented relative to each other to emit respective light beams that converge at a predetermined distance in front of the UV lamp.

2. The sanitizing head of claim 1, wherein the housing includes a shroud that defines a front opening, and the range light sources are spaced apart along an exposed perimeter edge of the shroud at the front opening.

3. The sanitizing head of claim 2, wherein the exposed perimeter edge is rectangular and includes two longer segments that extend between two shorter segments, the range light sources disposed on the two longer segments.

4. The sanitizing head of claim 2, wherein the exposed perimeter edge includes multiple segments, and the range light sources in each respective pair of the one or more pairs are disposed on a common segment of the multiple segments.

5. The sanitizing head of claim 1, wherein the light beams emitted by the range light sources in each pair have different colors.

6. The sanitizing head of claim 1, wherein the range light sources are light emitting diodes (LEDs) that have a divergence no greater than 10 degrees.

7. The sanitizing head of claim 1, wherein the range light sources in each pair are oriented at an angle in a range between 20 degrees and 60 degrees relative to each other.

8. The sanitizing head of claim 1, wherein the one or more pairs includes multiple pairs arranged in a first subset of one or more pairs and a second subset of one or more pairs, wherein the range light sources in each pair within the first subset are oriented at a first relative angle and the range light sources in each pair within the second subset are oriented at a second relative angle that is different from the first relative angle.

9. The sanitizing head of claim 8, wherein the first relative angle is at least 40 degrees and no greater than 60 degrees, and the second relative angle is at least 20 degrees and less than 40 degrees.

10. The sanitizing head of claim 9, wherein the first relative angle is approximately 53 degrees, and the second relative angle is approximately 28 degrees.

11. The sanitizing head of claim 1, wherein the predetermined distance is no less than 1 inch and no greater than 6 inches.

12. The sanitizing head of claim 1, wherein the UV lamp is configured to emit UV light having a wavelength between 200 nm and 280 nm.

13. The sanitizing head of claim 12, wherein the UV lamp is configured to emit UV light having a wavelength of approximately 222 nm.

14. The sanitizing head of claim 12, wherein the UV lamp is configured to emit UV light having a wavelength of approximately 254 nm.

15. A portable sanitizing method comprising:
emitting ultraviolet (UV) light from a sanitizing head including a housing and a UV lamp; and
emitting a first light beam from a first range light source on the sanitizing head and a second light beam from a second range light source on the sanitizing head to cause the first and second light beams to converge at a predetermined distance from the UV lamp, wherein the first range light source and the second range light source emit visible light.

16. The portable sanitizing method of claim 15, wherein the first light beam and the second light beam have different colors.

17. The portable sanitizing method of claim 15, further comprising mounting the first and second range light sources at a relative angle on the housing to cause the first and second light beams to converge at a predetermined distance that is no less than 1 inch and no greater than 6 inches from the UV lamp.

18. The portable sanitizing method of claim 15, further comprising mounting multiple pairs of the range light sources along a housing of the sanitizing head in two parallel rows with the UV lamp disposed between the two parallel rows.

19. The portable sanitizing method of claim 15, wherein the first and second range light sources represent a pair within a first subset of one or more pairs of range light sources, and the method further comprises deactivating the first subset and activating a second subset of one or more pairs of the range light sources, the one or more pairs in the second subset having a different relative angle between the range light sources than the one or more pairs in the first subset.

20. A sanitizing head comprising:
a housing that retains an ultraviolet (UV) lamp configured to emit UV light, the housing including a shroud that defines a front opening; and
multiple range light sources secured to the housing and spaced apart along an exposed perimeter edge of the shroud at the front opening, the range light sources arranged in one or more pairs, wherein the range light sources emit visible light, the range light sources in each pair oriented relative to each other to emit respective light beams that converge at a predetermined distance in front of the UV lamp, wherein the range light sources are light emitting diodes (LEDs) that have a divergence no greater than 10 degrees, and the light beams emitted by the range light sources in each pair have different colors.

21. The sanitizing head of claim 20, wherein the one or more pairs includes multiple pairs arranged in a first subset of one or more pairs and a second subset of one or more pairs, wherein the range light sources in each pair within the first subset are oriented at a first relative angle and the range light sources in each pair within the second subset are oriented at a second relative angle that is different from the first relative angle.

* * * * *